Figure 1:
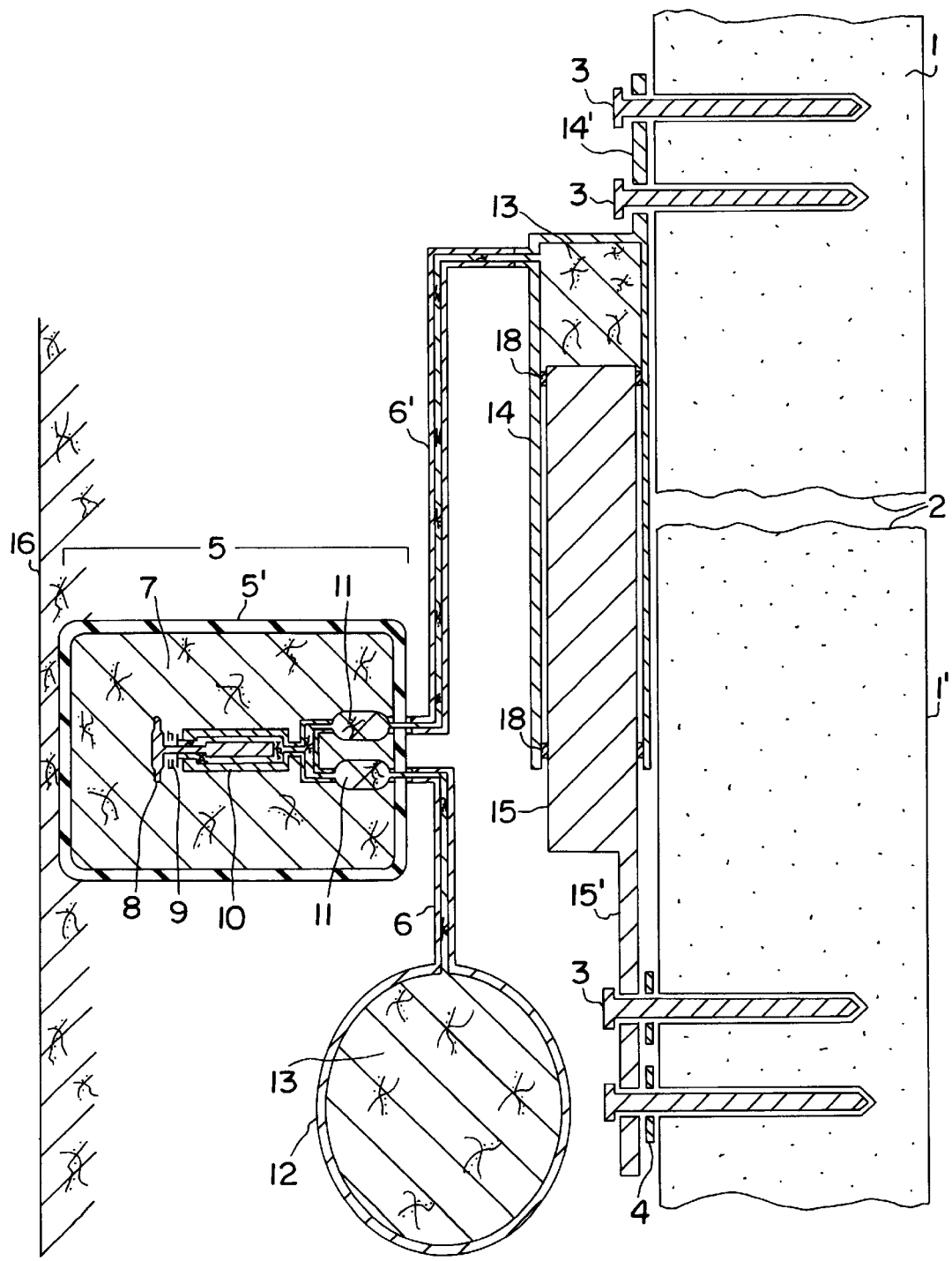

United States Patent [19]
Sachse

[11] Patent Number: 6,106,525
[45] Date of Patent: Aug. 22, 2000

[54] FULLY IMPLANTABLE BONE EXPANSION DEVICE

[76] Inventor: Hans Sachse, Lerchenstrasse 55, 90425 Nuernberg, Germany

[21] Appl. No.: 09/157,595

[22] Filed: Sep. 21, 1998

[30]  Foreign Application Priority Data

Sep. 22, 1997 [DE] Germany .................. 197 41 757

[51] Int. Cl.⁷ .................................................. A61B 17/56
[52] U.S. Cl. ............................................................ 606/59
[58] Field of Search .................. 606/68, 69, 70, 606/71, 57, 58, 105, 241

[56] References Cited

U.S. PATENT DOCUMENTS 2,391,693  12/1945  Ettinger ........................... 606/59
3,976,060  8/1976  Hildebrandt et al. ............... 606/241
4,157,715  6/1979  Westerhoff ......................... 606/60

Primary Examiner—Michael Buiz
Assistant Examiner—Jackie Tan-Uyen T. Ho
Attorney, Agent, or Firm—Keil & Weinkauf

[57]  ABSTRACT

This invention describes a bone lengthening device, which is fully implantable and works on a cylinder and piston basis which is driven with micro-hydraulics or a internal threaded rod. Choosing a profile which is not round, torsion of the cylinder and piston assembly is avoided, and expansion can be achieved both in a linear as well as in a circular fashion. Since this device is fully implantable, common disadvantages with current methods of bone expansion can be eliminated.

13 Claims, 2 Drawing Sheets

FULLY IMPLANTABLE BONE EXPANSION DEVICE

The invention describes an implantable expansion device to lengthen bone. Recently, the lengthening of bone has become a more common procedure in medicine. To achieve such a lengthening, the following procedure is typically followed: Initially the bone is transsected in its middle aspect. Then, both parts are slowly distracted with a special device until the desired length has been obtained. Then, the bone ends are maintained at this distance until osseous consolidation has been achieved. During this entire process, both ends of the bone have to be fixated in the correct position and in the correct distance to obtain controlled bone growth.

The typical device for this purpose consists of two or more sets of bone-anchors which are attached with a set of clamps to guiding bars, which can be separated with a threaded rod. The distance between the bone ends can be varied by turning the threaded bar. Usually, these devices which have become known as bone expanders, are located externally, outside the body. In this case, screws/bone anchors penetrate the skin and the underlying soft tissue to reach the bone. Another option which has been used recently clinically has most pieces lying within the soft tissues overlying the bone, with only one rod penetrating the skin to operate the threaded rod which is used to increase the distance between the afore mentioned bone anchors.

An alternative to bone anchors and screws had been developed by Illizarov, who used percutaneous tensed wires which were attached to a frame instead of the percutaneous screws. Both linear as well as rotational motion are possible by manipulation of the often rather bulky external frame.

All of the above mentioned devices have a substantial common disadvantage: They penetrate the skin and form a track, which exposes the wound and the underlying bone to bacterial invasion and infection which may necessitate the abandonment of the bone lengthening procedure. Additionally, the scars at the entry site of the bone anchors which form during the expansion process are known to be usually extensive and quite disfiguring.

It is the purpose of the device described in this invention to achieve controlled bone lengthening without the risk of infection by percutaneous wounds or significant scarring.

To achieve this task, this system is based on a microhydraulic system, which can be placed completely in the soft tissues and has no connection to the external surface (skin and mucuos membranes), thus eliminating or minimizing the risk of infection. Similar subcutaneous hydraulic systems are already known in urology for sphincter prosthesis as described by Scott as well as for penile prostheses. In this invention, the expander is typically driven by a small hydraulic pump, which is manipulated by pressure transmitted through the skin. This results in a defined increase of the distance between the bone anchors. Alternatively, a small implantable electrical pump can be used to enpower the hydraulic expander. Another option exists in moving the hydraulic fluid through thin percutaneous tubing, which has the disadvantage that a small connection between the subcutaneous tissue and the external surface remains. Nevertheless, due to the substantially smaller wound and the possibility to locate the perforation for the tubing far away from the expansion site, this still presents a substantial improvement over current devices. In another option, the piston of the expansion device is moved with a threaded rod, which is moved by a geared electric motor.

Further advantages and properties of the invention may be obtained from the claims of the subsequent description and drawings of the preferred example.

DESCRIPTION

The schematic drawings of the preferred embodiments show:

FIG. 1: Longitudinal view of the implantable bone expansion device.

Figure 2:
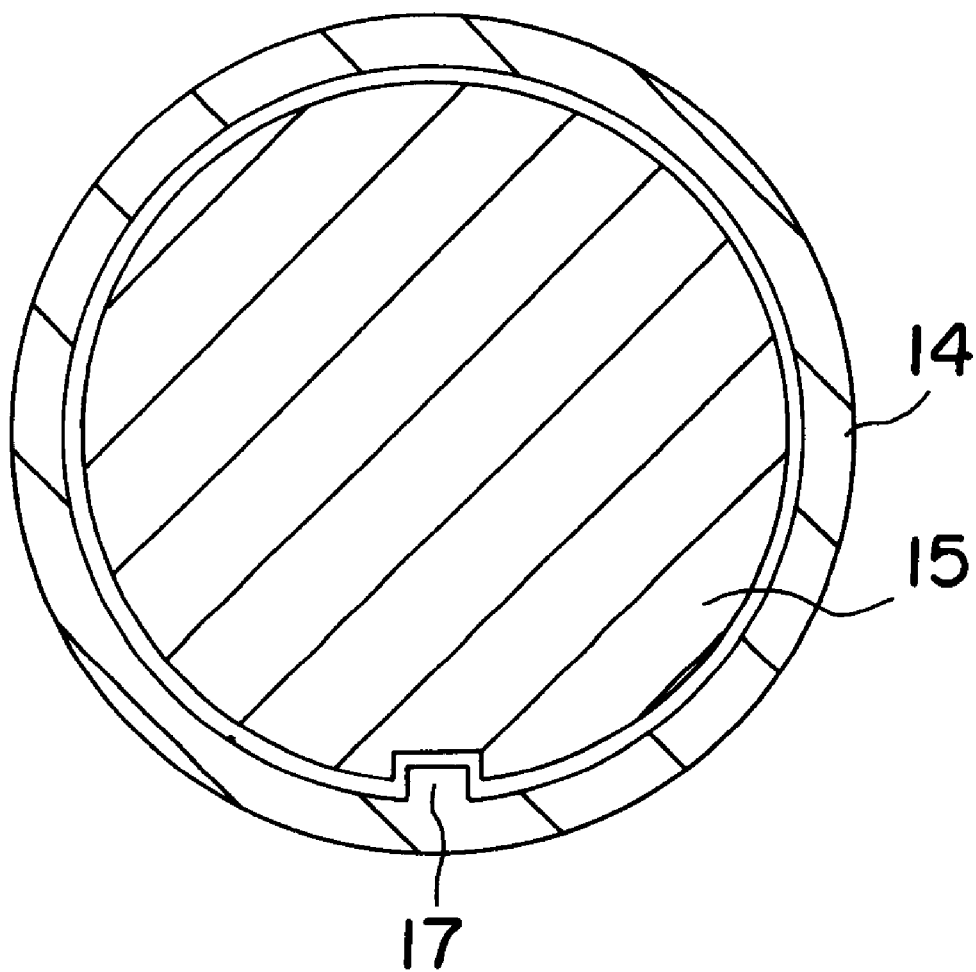

FIG. 2: Cross-sectional view through the expansion-cylinder and piston 14.

The bone expansion device consists of a hydraulic cylinder 14, which is connected to a clamping mechanism 14' which holds 2 bone anchors 3 which are attached to the bone segment 1. Hydraulic fluid 13 forces the piston 15 to slide inside the hydraulic cylinder 14. Similar to the hydraulic cylinder 14 the piston 15 is attached to a clamping mechanism 15' which is attached as well to bone anchors 3 which are attached to the second bone segment 1'. The bone segments 1 and 1' are separated by the distraction zone 2 where distraction osteoneogenesis takes place. The controlled volume of hydraulic fluid 13, which moves the piston 15 out of the hydraulic cylinder 14, is achieved by the hydraulic pump 5 which is inside an elastic cover 5' which is filled with gel or fluid 7. This hydraulic pump obtains its hydraulic fluid 13 through a tube 6 from a reservoir 12. Valves 11 direct the hydraulic fluid which is moved with the help of pump-piston 8, spring 9 and pump housing 10. The hydraulic pump 5 is connected with tubing 6' with the hydraulic cylinder 14. Through the skin 16 and the elastic cover 5' pressure can be transmitted to the pump piston 8. Hereby the hydraulic fluid 13 is pressed in controlled quantities into the lumen of the hydraulic cylinder 14. Thus, the piston 15 is moved out of the hydraulic cylinder 14 and distracts bone segments 1 and 1'. A sealing mechanism 18 eliminates leaks of the biocompatible hydraulic fluid 13 between the hydraulic cylinder 14 and the piston 15.

FIG. 2: A bar 17 is attached to the inside of the expansion cylinder 14 to eliminate rotation of the piston 14 against the cylinder 15.

What is claimed is:

1. A device for expansion and fixation of two bone segments, consistent of a cylinder and a piston which cylinder has a fixation mechanism at both ends to attach these to the bone segments, and produced from biologically tolerated and compatible materials, wherefor the entire device can be implanted in the soft tissues wherein the cylinder has a round internal diameter, wherein the interior surface has a longitudinal bar and the piston an accompanying gap, thus eliminating rotation between the piston and cylinder assembly.

2. An instrument according to claim 1, wherein the expander is driven by a hydraulic pump which is as well implanted in the soft tissues and obtains its energy and regulation from percutaneous manipulation.

3. Instrument according to claim 1, wherein the expander is driven by a small implantable electrical hydraulic pump.

4. A device according to claim 1, wherein the electrical pump is controlled through a switch or an electronic device which can be controlled and operated through the skin.

5. A device according to claim 1, wherein an electric pump is driven through percutaneous magnetic induction.

6. A device with a cylinder with a round internal diameter, wherein the interior surface has a longitudinal bar and the piston an according gap, thus eliminating rotation between the piston and cylinder assembly.

7. A device according to claim 1, wherein the cylinder and the piston have a profile which is not round, thus eliminating rotation of the piston against the cylinder.

8. A device according to claim 7, wherein the rotation of the piston against the cylinder is eliminated through an external structure, which is parallel to the piston and cylinder.

9. A device according to claim 1, wherein the piston and cylinder are not straight but are curved, thus resulting in a circular motion and bone expansion along a curve.

10. A device according to claim 1, wherein the hydraulic pump is driven through injection in a subcutaneous reservoir.

11. A device according to claim 1, wherein overexpansion is avoided by an end-block and an overflow slit in the cylinder.

12. A device according to claim 1, wherein an expandable container is placed between the piston and (hydraulic) cylinder, thus eliminating need for seals.

13. A device according to claim 1, wherein the piston inside the cylinder is not driven by hydraulic fluid but by a threaded rod which is driven by a small geared electric motor.

* * * * *

UNITED STATES PATENT AND TRADEMARK OFFICE
CERTIFICATE OF CORRECTION

PATENT NO.    : 6,106,525                                  Page 1 of 1
DATED         : August 22, 2000
INVENTOR(S)   : Hans Sachse It is certified that error appears in the above-identified patent and that said Letters Patent is hereby corrected as shown below:

<u>Column 2,</u>
Line 53, "or an electronic" should be -- or the electronic --.
Cancel claim 6 (lines 57-59).
Line 62, "the piston" should be -- the accompanying piston --.

<u>Column 4,</u>
Cancel claim 13 (lines 4-8).

Signed and Sealed this

Fourteenth Day of August, 2001

*Attest:*

*Attesting Officer*

NICHOLAS P. GODICI
*Acting Director of the United States Patent and Trademark Office*